(12) United States Patent
Asselbergs et al.

(10) Patent No.: US 6,963,068 B2
(45) Date of Patent: Nov. 8, 2005

(54) METHOD FOR THE MANUFACTURE AND TRANSMISSIVE IRRADIATION OF A SAMPLE, AND PARTICLE-OPTICAL SYSTEM

(75) Inventors: Peter Emile Stephan Joseph Asselbergs, Eindhoven (NL); Hendrik Gezinus Tappel, Casteren (NL); Gerard Nicolaas Anne van Veen, Waalre (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 10/758,651

(22) Filed: Jan. 15, 2004

(65) Prior Publication Data

US 2004/0144924 A1 Jul. 29, 2004

(30) Foreign Application Priority Data

Jan. 17, 2003 (NL) .................................... 1022426

(51) Int. Cl.$^7$ ........................ H01J 37/30; H01J 37/26; G01N 1/28
(52) U.S. Cl. ...................... 250/311; 250/307; 250/309; 250/310; 250/492.2; 250/492.21
(58) Field of Search ................... 250/307, 311, 492.21, 250/310, 306, 309, 492.2

(56) References Cited

U.S. PATENT DOCUMENTS

| | | | |
|---|---|---|---|
| 5,270,552 A | 12/1993 | Ohnishi et al. | |
| 5,525,806 A | 6/1996 | Iwasaki et al. | |
| 5,656,811 A | 8/1997 | Itoh et al. | |
| 5,986,264 A | 11/1999 | Grunewald | |
| 6,188,068 B1 * | 2/2001 | Shaapur et al. | ............. 250/307 |
| 6,376,839 B1 | 4/2002 | Hayles et al. | |
| 6,417,512 B1 | 7/2002 | Suzuki | |
| 6,538,254 B1 * | 3/2003 | Tomimatsu et al. | ..... 250/442.11 |
| 6,664,552 B2 * | 12/2003 | Shichi et al. | .......... 250/492.21 |
| 6,717,156 B2 | 4/2004 | Sugaya et al. | |
| 6,781,125 B2 * | 8/2004 | Tokuda et al. | ............... 250/310 |
| 6,828,566 B2 | 12/2004 | Tomimatsu et al. | |
| 2002/0050565 A1 * | 5/2002 | Tokuda et al. | ............... 250/310 |
| 2002/0166976 A1 | 11/2002 | Sugaya et al. | |
| 2003/0183776 A1 | 10/2003 | Tomimatsu | |
| 2004/0144924 A1 | 7/2004 | Asselbergs et al. | |
| 2004/0178372 A1 | 9/2004 | Rasmussen | |

FOREIGN PATENT DOCUMENTS

| | | |
|---|---|---|
| EP | 0 687 897 A1 | 6/1995 |
| EP | 0 927 880 A1 | 7/1998 |
| EP | 1 473 560 A1 | 11/2004 |
| JP | 2002 062226 | 2/2002 |
| JP | 2002062226 | 2/2002 |

* cited by examiner

Primary Examiner—Nikita Wells
Assistant Examiner—Johnnie L Smith, II
(74) Attorney, Agent, or Firm—Michael O. Scheinberg

(57) ABSTRACT

The invention provides a method for the manufacture and transmissive irradiation of a sample, comprising the steps of:
A Providing a particle-optical system having an internal low-pressure chamber and suitable for the generation of an electron beam and an intersecting ion beam in said chamber;
B Providing a specimen within the chamber, carried by a manipulator;
C Irradiating the specimen with the ion beam so as to cut a sample from the specimen;
D Relatively displacing the sample thus cut to a sample holder than can be manipulated;
E Attaching the sample to the sample holder;
F Using an electron beam to perform transmissive irradiation of the sample thus attached to the sample holder, characterized in that step F is performed in the low-pressure chamber of the particle-optical system according to step A.

40 Claims, 10 Drawing Sheets

Figure 1:
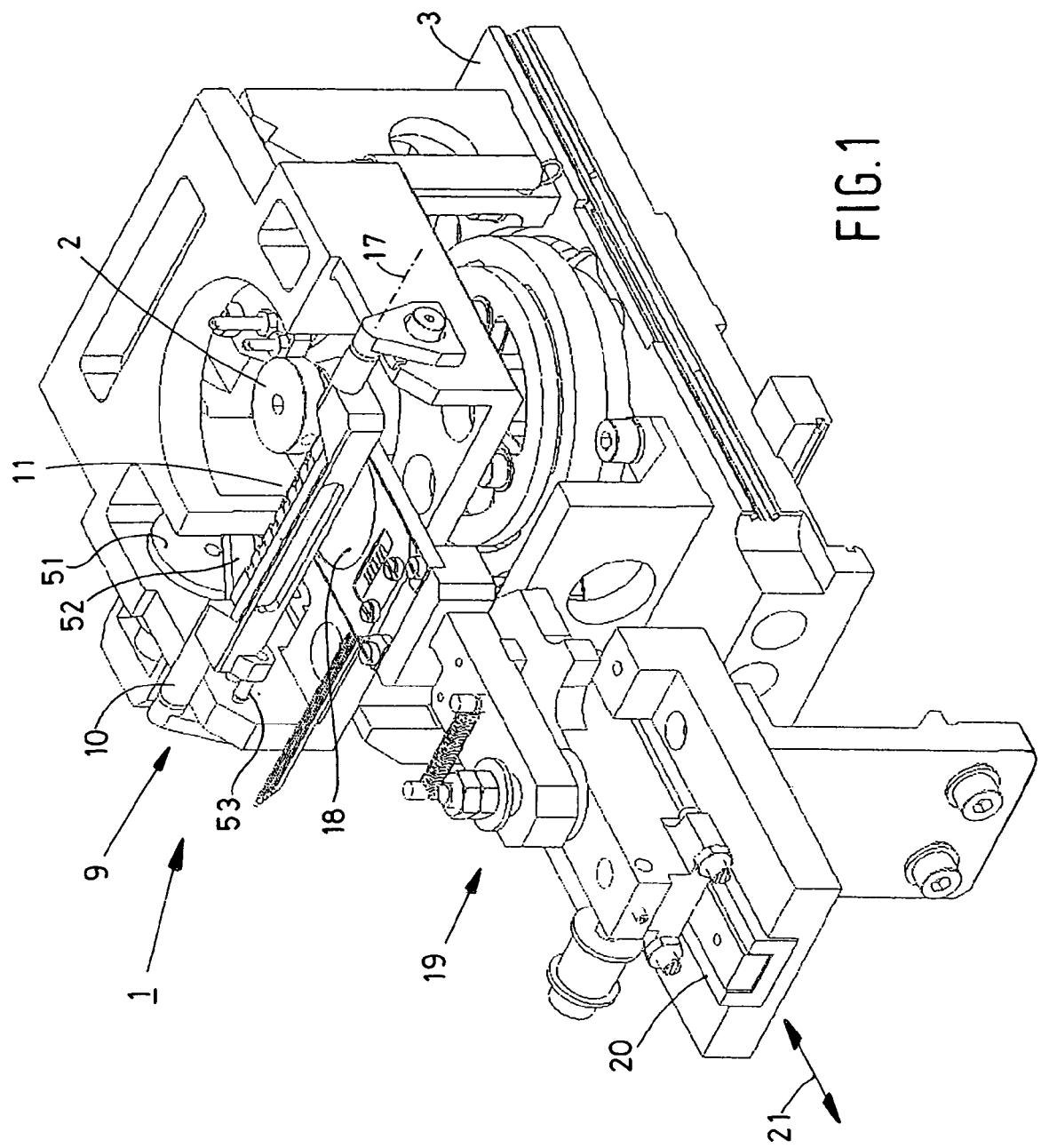

METHOD FOR THE MANUFACTURE AND TRANSMISSIVE IRRADIATION OF A SAMPLE, AND PARTICLE-OPTICAL SYSTEM

The invention relates to a method for the manufacture and transmissive irradiation of a sample, comprising the steps of:

A Providing a particle-optical system having an internal low-pressure chamber and suitable for the generation of an electron beam and an intersecting ion beam in said chamber;
B Providing a specimen within the chamber, carried by a manipulator;
C Irradiating the specimen with the ion beam so as to cut a sample from the specimen;
D Relatively displacing the sample thus cut to a sample holder than can be manipulated;
E Attaching the sample to the sample holder;
F Using an electron beam to perform transmissive irradiation of the sample thus attached to the sample holder.

In the field of electron microscopy, one can introduce a rough distinction between scanning electron microscopy (SEM) and transmission electron microscopy (TEM). Both technologies have their own specific advantages and disadvantages, which inter alia determine their specific areas of application. An important common factor is formed by the fact that, in both technologies, use is made of an electron beam that, as a result of an accelerative voltage, is directed within a low-pressure chamber at an object to be investigated. A typical accelerative voltage for a SEM is 30 kV, whereas a typical accelerative voltage for a TEM is 300 kV. This higher accelerative voltage for a TEM is necessary so as ensure that electrons in the electron beam are at least partially irradiated through the object to be investigated. To this end, it is also necessary that an object to investigated using a TEM have a certain maximal thickness, which is normally around 100 nm. As a result of the differences that exist between SEM technology and TEM technology, one can conclude that SEMs are more widely applied, inter alia as a result of their lower price, whereas TEMs are proportionately less widely applied, inter alia because of the more highly trained personnel needed for their operation and, as already referred to, the required special preparation of the object to be investigated.

One can, however, conclude that SEM and TEM technology are demonstrating a convergence. A good example of this is formed by so-called scanning transmissive electron microscopy (STEM), whereby, in a SEM environment (characterized by a relatively low accelerative voltage), an electron detection plate is provided under a sample, which plate allows an image of the sample to be obtained. In this scenario, use is made of the fact that the degree of deflection suffered by an electron during irradiation through a sample is dependent on the mass of the elements that an electron passes during the irradiation. The contrast mechanism thus created generates the image of the sample. In this context, reference is made to U.S. Pat. No. B1-6,376,839.

A method according to the opening paragraph is known from European patent application EP 927880 A1 in which, in the first instance, an extensive dissertation is given with regard to manners in which an object can be made suitable for study using a TEM. To this end, the object should be in the form of a TEM sample with a certain maximal thickness of approximate magnitude 100 nm. In said European patent application, the fifth embodiment describes, according to the prior art, a method and accompanying apparatus for the manufacture of a TEM sample. In brief, this TEM sample is produced by irradiating an object with an ion beam in a vacuum chamber, by means of which a thin portion of this object is cut off. Using a probe on whose tip the cut off portion is attached using metal deposition, the cut off portion is move away from the object from which it was cut off and transferred to a TEM sample holder. In this TEM sample holder, the cut off portion—which can be regarded as the TEM sample in crude form—is further thinned using further irradiation by an ion beam, until such time as the desired thickness is reached. After this preparation, the TEM sample holder, together with the TEM sample attached thereto, is removed from the vacuum chamber, for which purpose an air lock chamber, for example, can be provided. In a subsequent step, the TEM sample holder and TEM sample are introduced into the vacuum chamber of a TEM, so as to undergo further investigation there by irradiating an electron beam through the TEM sample.

An important disadvantage of the method and apparatus according to the prior art described above is that, after preparation, the sample is exposed to the outside atmosphere, as a result of which, for example, unwanted oxidation of the sample can occur.

The invention aims to provide a significant alleviation of the described disadvantages of the prior art, whether or not in preferential embodiments. More particularly, the invention aims to provide a method that makes it easier to apply TEM-like techniques, such as STEM technology, in a SEM environment, whereby the various required actions can be carried out by personnel with a lower level of training than the personnel used to operate TEM apparatus to date. It is hereby estimated that investigations that, in the prior art, are often carried out with a TEM could, in a large number of cases and with all attendant advantages, also be carried out with a SEM microscope, on the condition that the latter were provided with the correct options.

In the light of the dissertation above, the method according to the invention is characterized in the first instance in that step F is performed in the low-pressure chamber of the particle-optical system according to step A. The enormous advantage achieved in this manner is that, after the sample has been prepared, it is no longer necessary to expose it to a detrimental atmosphere, or, using complex transfer means provided for this purpose, to transfer it from the low-pressure chamber in which preparation was performed to a chamber of another particle-optical system where the transmissive irradiation of the sample with an electron beam is to take place.

The advantages of the invention are especially achieved if, during step F, an electron detection surface is positioned at the side of the sample opposite to the electron beam. Such an electron detection surface can be part of STEM apparatus.

A further preferential embodiment of the method according to the invention is achieved if, after executing step E, the sample is irradiated with the ion beam, for the purpose of further processing the sample. Such further processing will in practice particularly comprise the optimization of the thickness of the sample.

So as to make it possible to perpendicularly irradiate the sample in the sample holder using both the electron beam and the ion beam, which subtend an angle with one another, it is preferable, after execution of step E, that the sample holder be rotated about a rotational axis that is perpendicular to the electron beam and to the ion beam.

Said rotational axis preferably extends through the point of intersection of the electron beam and the ion beam, since, in that case, it is not necessary to continually focus the electron beam and/or the ion beam after or during rotation.

So as to make it possible to perform irradiation on opposite sides of the sample—particularly by the electron beam, but also, if desired, by the ion beam—rotation about the rotational axis is performed, possibly in combination with rotation about a manipulator rotational axis that extends parallel to said rotational axis, through a range of at least 180 degrees.

The invention further relates to a particle-optical system, particularly for application in conjunction with a method according to the invention as described above. In accordance with the prior art as set forth in the European application EP 927880 A1, and more specifically the fifth embodiment that is described therein, the particle-optical system comprises a low-pressure chamber containing manipulator means for at least two objects to be irradiated, an electron source and an ion source for the purpose of allowing irradiation of an object, carried by the manipulating means, using an electron beam and an ion beam, respectively, the manipulating means comprising a number of first manipulation parts, which are movable relative to one another and collectively movable relative to the electron beam and the ion beam according to a first set of degrees of freedom, an extremal one of which first manipulation parts comprises a first object carrier, for allowing, in the case of a first object carried by the first object carrier and at a first position of the manipulating means, reflective irradiation of said first object using an electron beam and/or irradiation of said first object using an ion beam, the manipulating means further comprising at least one second manipulation part comprising a second object carrier, the system further comprising displacing means for relatively displacing an object from the first object carrier to the second object carrier.

In the case of the system according to the fifth embodiment described in EP 927880 A1, a manipulator—which in common jargon in the field is also referred to as a "stage"—is part of the manipulating means. From a wafer, or a loose piece thereof, which is carried by the manipulator, a TEM sample can be cut off using an ion beam, which sample can subsequently be transferred using a probe to a TEM sample holder that is connected in a removable manner to the stage at the edge of the range of the stage but within the region of the electron beam and the ion beam. As already described, the TEM sample holder is removed from the preparation chamber so as to be investigated in another particle-optical system. The disadvantages associated herewith have already been described above. Apart from a method, the invention also aims to provide a particle-optical system whose use allows these disadvantages to be overcome. To this end, the system according to the invention is characterized in the first instance in that the manipulating means are embodied so as to allow, in the case of a second object carried by the second object carrier and at a second position of the manipulating means, transmissive or reflective irradiation of said second object by an electron beam and/or irradiation of said second object by an ion beam. As a result of this specific arrangement of the manipulating means in accordance with the invention, it is possible, in one and the same vacuum chamber, to manufacture a sample in a first position of the manipulating means and to investigate this sample, using a particle beam, in a second position of the manipulating means (whereby the sample can also be further processed in the second position, if desired). The advantages associated herewith have already been set forth above.

So as to have greater freedom with regard to the angle at which the particle beam concerned is directed at the sample, it is preferable that the second manipulation part be movable in at least one further degree of freedom with respect to the electron beam and the ion beam, as well as with respect to a remaining portion of the manipulating means.

A very advantageous embodiment thereof is obtained if said at least one further degree of freedom is a rotation about a rotational axis that extends perpendicular to the electron beam and to the ion beam, more preferably if the rotation about the rotational axis can occur through a range of at least 180 degrees—combined, if desired, with rotation about a manipulator rotational axis that extends parallel to said rotational axis—and even more preferably if the rotational axis extends through the point of intersection of the electron beam and the ion beam. The specific advantages of such preferential embodiments have already been set forth above on the basis of the corresponding preferential embodiments of the method according to the invention.

A particularly advantageous embodiment is obtained if the motion according to said at least one further degree of freedom can only occur in combination with motion according to one degree of freedom of the first set of degrees of freedom. This preferential embodiment is based on the insight that it is not disadvantageous to allow motion according to said at least one further degree of freedom to occur simultaneously with motion according to one of the degrees of freedom of the first set of degrees of freedom, seeing as, at a given instant, either only a first object carried by the first object carrier, or only a second object carried by the second object carrier, can be irradiated by a particle beam. Attendant hereto is the important advantage that the embodiment of the manipulating means can remain simple, since it is not necessary to make separate provision for mutually independent enaction of the movements according to said at least one further degree of freedom and according to one of the degrees of freedom of the first set of degrees of freedom. This means that, in principle, it is also relatively easily possible to add to the stage a second manipulation part that can be bent—according to at least one further degree of freedom—with respect to the electron beam and the ion beam, as well as with respect to the remainder of the degrees of freedom.

As already elucidated in connection with a corresponding preferential embodiment of a method according to the invention, a preferential embodiment of a system according to the invention is characterized in that the system comprises an electron detection surface at the side of the second object—carried by the second object holder—that is remote from the electron beam.

From a constructional point of view, it is further preferable that the electron detection surface be collectively movable with the manipulating means, in the direction extending between the first position and the second position of the manipulating means, since, in this scenario, no separate arrangements have to be made to achieve the collective movement. In this manner, it is, for example, possible to add the electron detection surface to an existing manipulator in a suitable and—more importantly—simple manner.

The preferential embodiment discussed above does not exclude a scenario whereby, in accordance with a further preferential embodiment, the electron detection surface and the manipulating means are movable independently of one another, in the direction extending between the first position and the second position of the manipulating means, as a result of which one obtains optimal freedom as regards mutual positioning.

According to an advantageous preferential embodiment, the resilience of spring means causes the electron detection surface to move together with the manipulating means from the first position to the second position, whereas a stopping contact between the manipulating means and a part rigidly connected to the electron detection surface causes the electron detection surface to move together with the manipulating means from the second position to the first position.

So as to ensure that, in the second position of the manipulating means, some amount of mutual movement is possible between the electron detection surface and the second manipulation part—or, more specifically, the second object carrier thereof, with the second object therein—it is of further advantage if, in the second position of the manipulating means, there is a certain play between the manipulating means and the part rigidly connected to the electron detection surface.

Figure 2A:
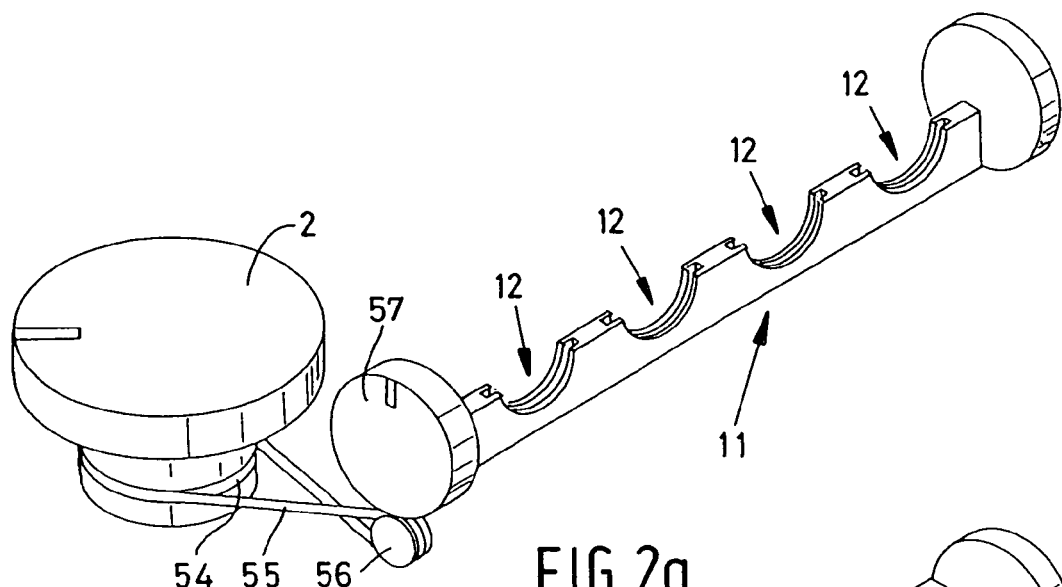
Figure 2B:
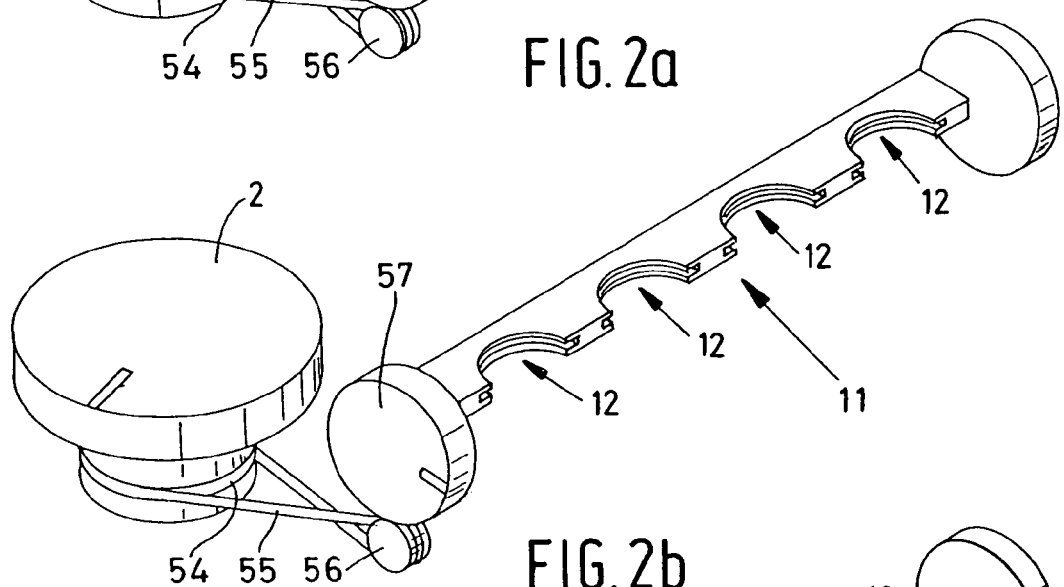
Figure 2C:
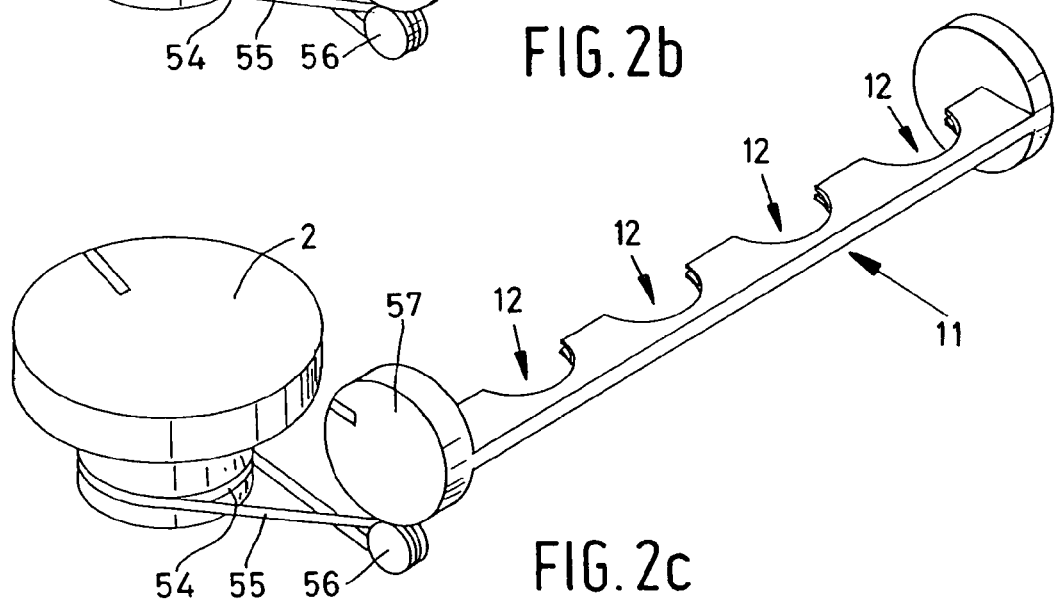
Figure 3:
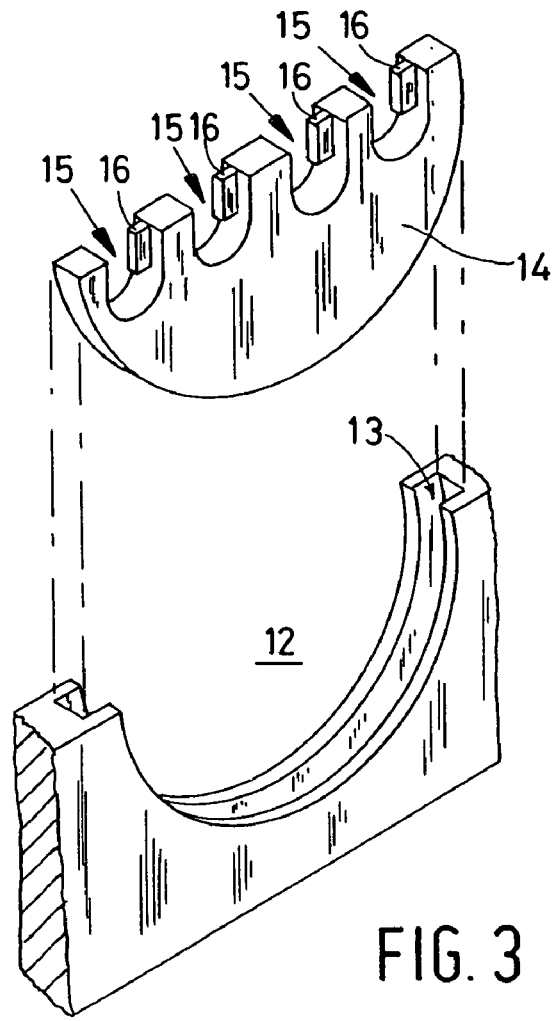
Figure 4:
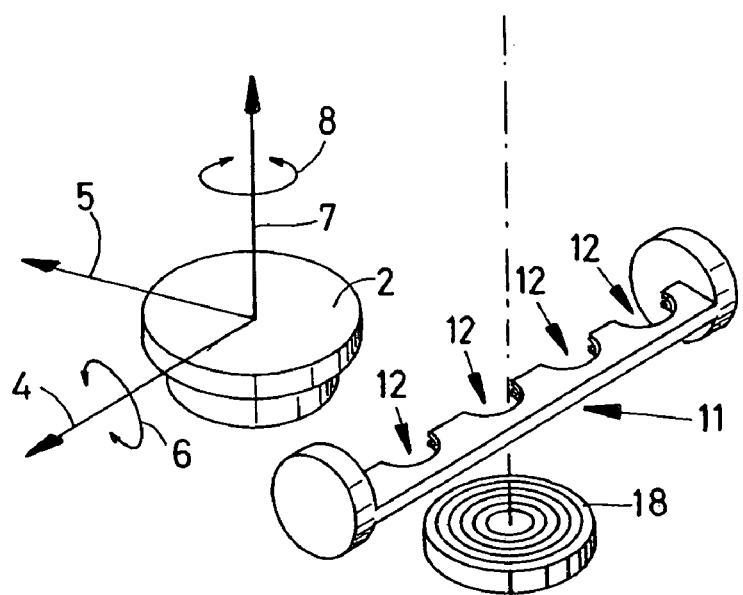
Figure 5A:
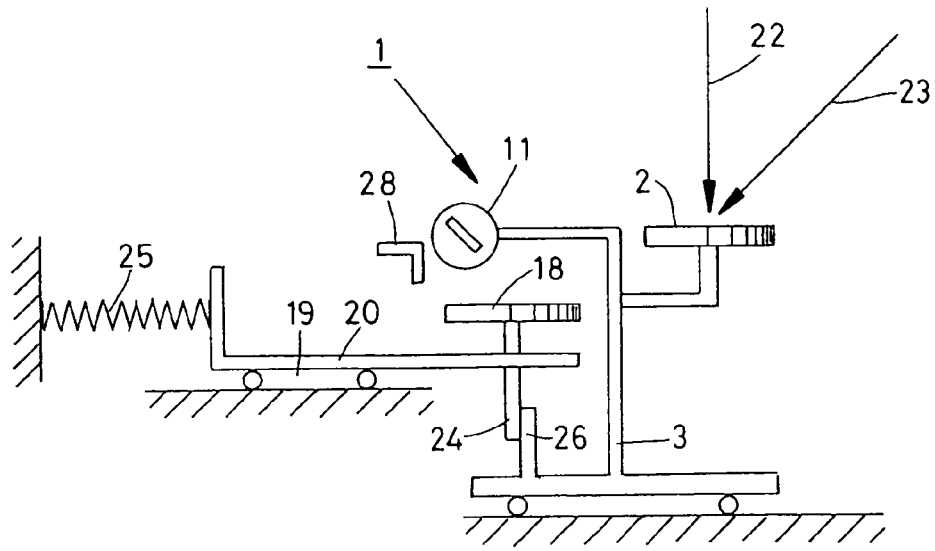
Figure 5B:
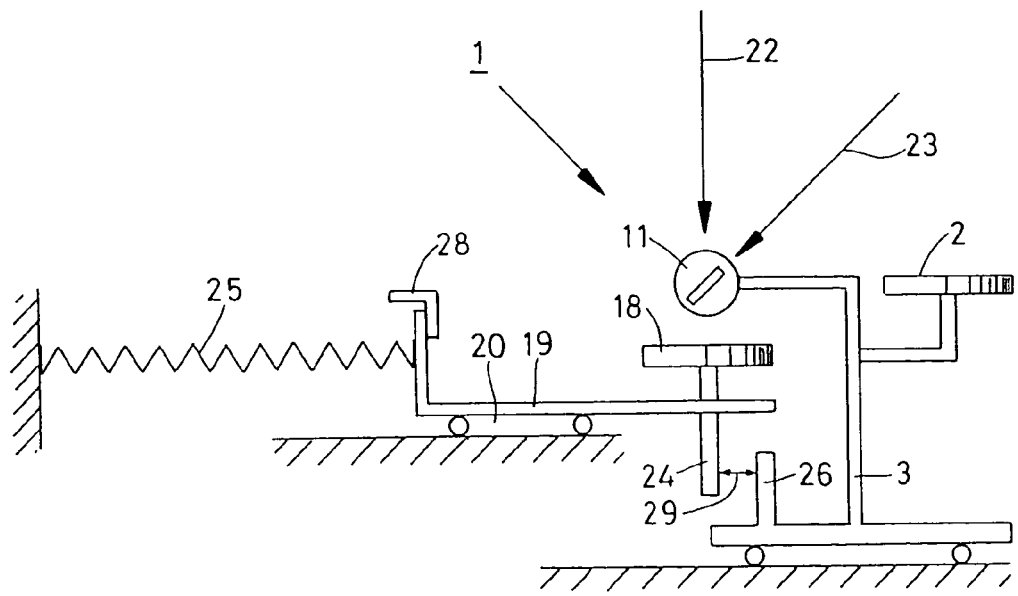
Figure 6:
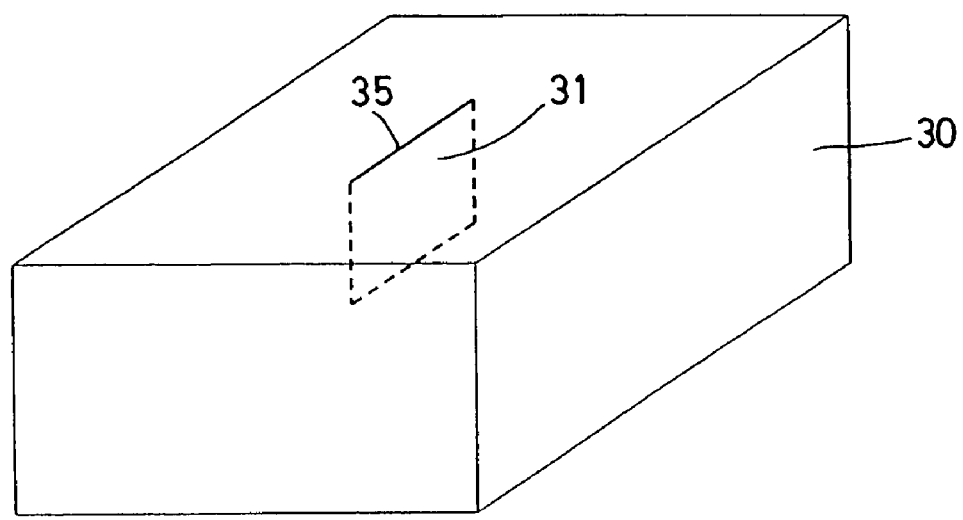
Figure 7:
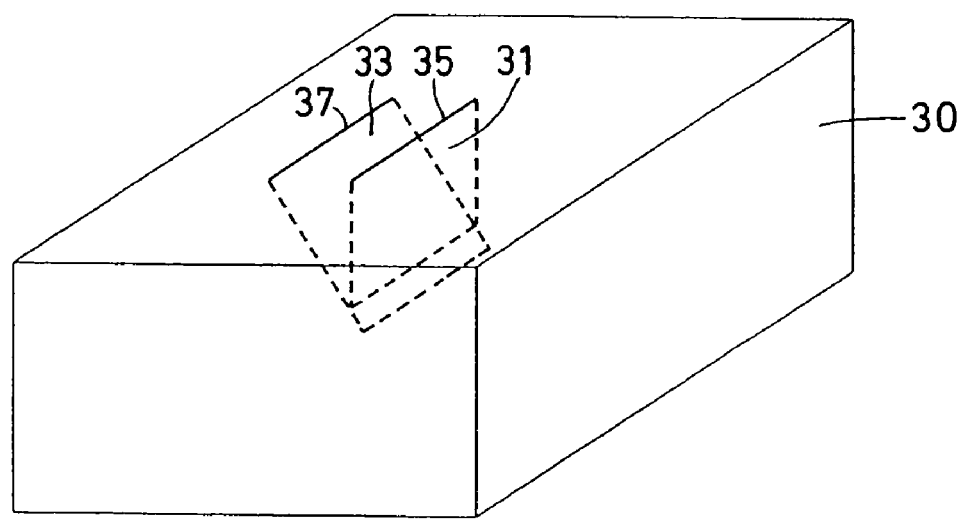
Figure 8:
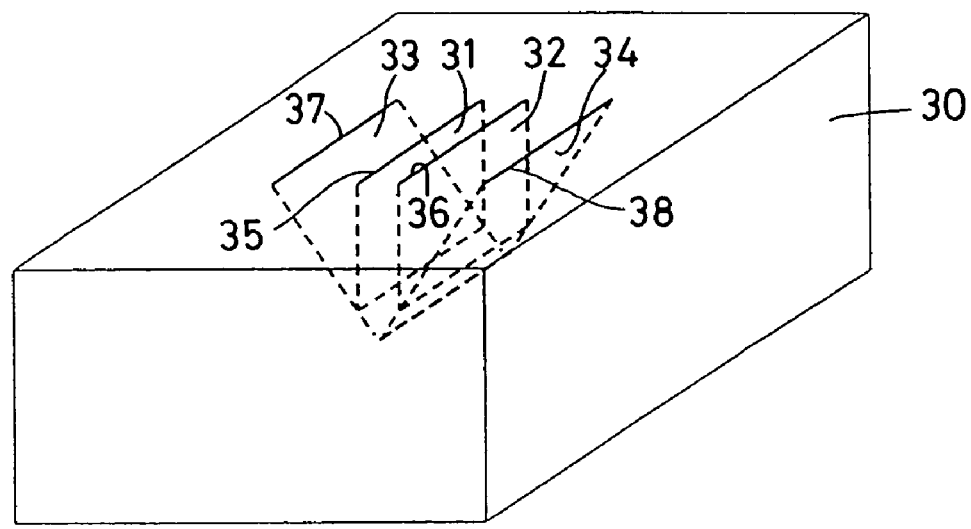
Figure 9:
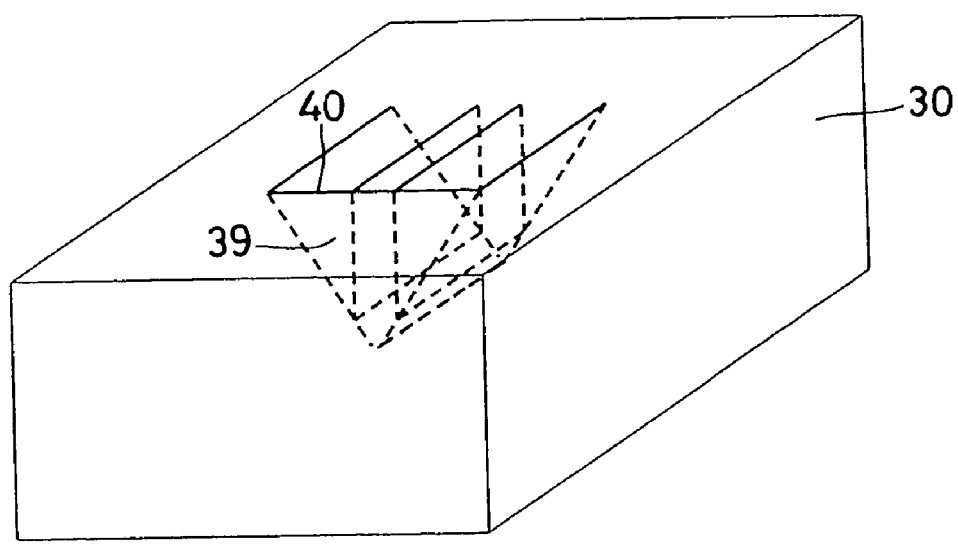
Figure 10:
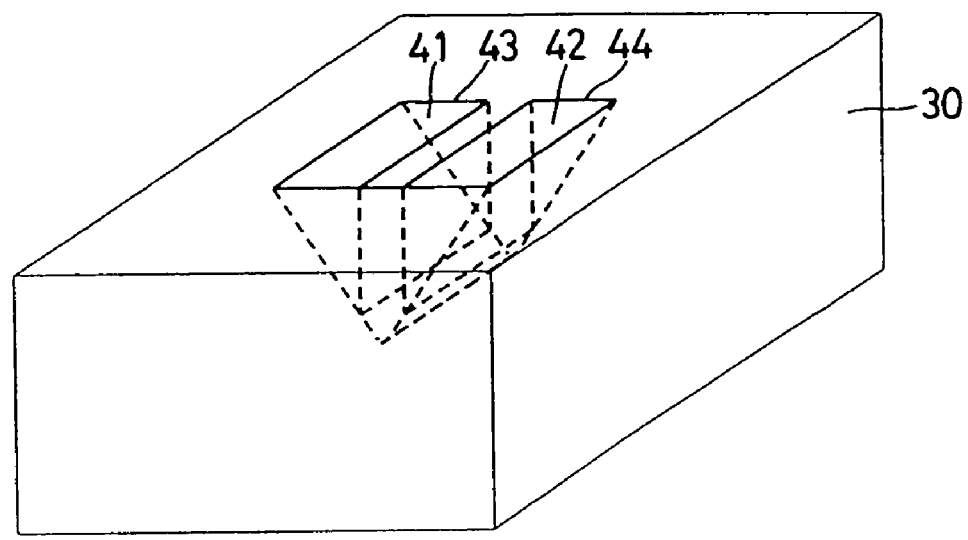
Figure 11:
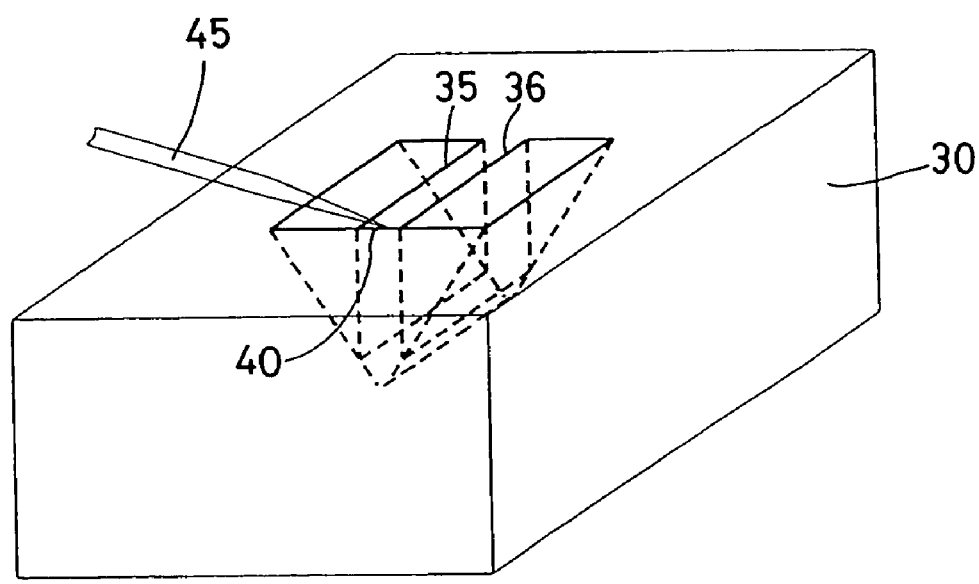
Figure 12:
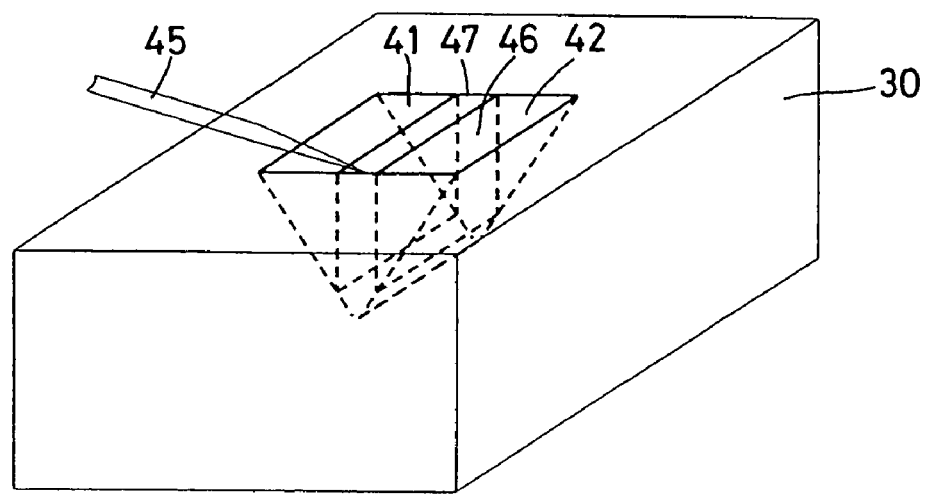
Figure 13:
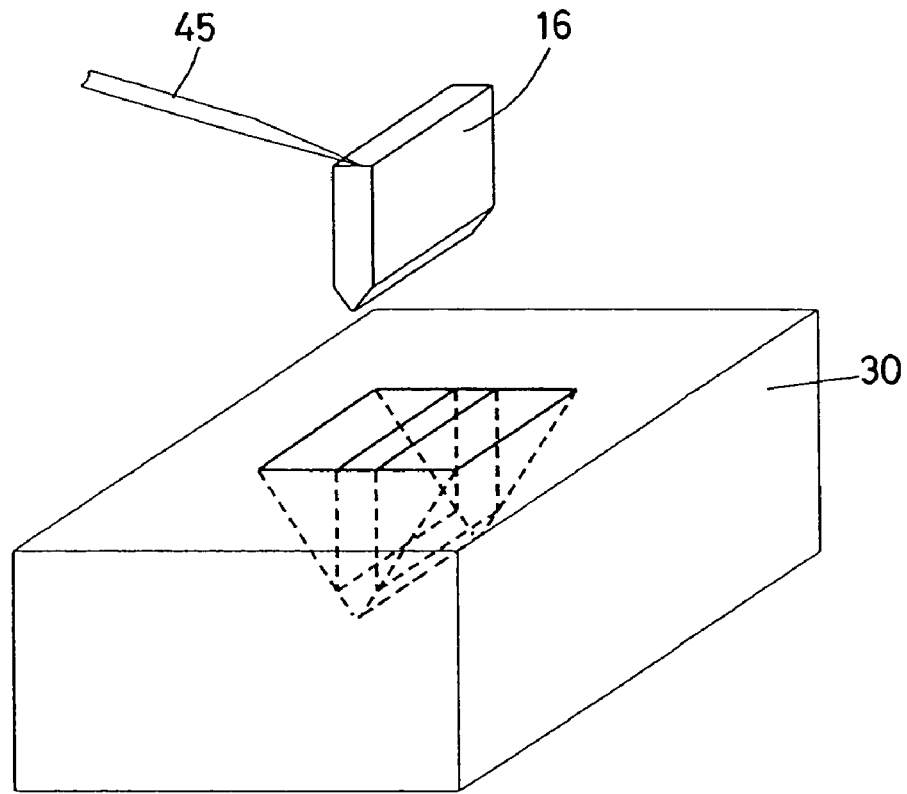
Figure 17A:
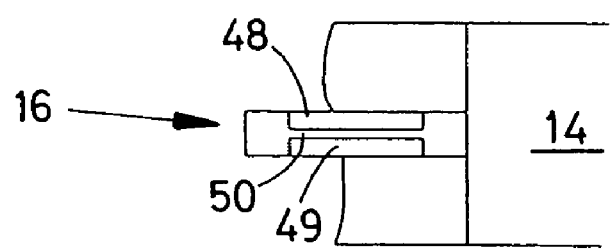
Figure 17B:
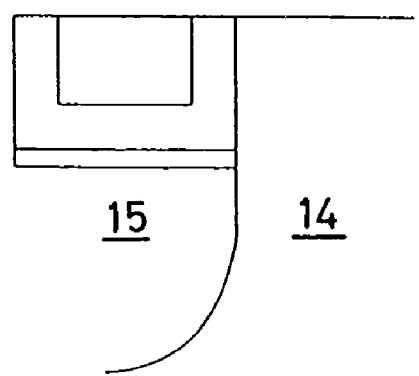

In what follows, the invention will be further elucidated on the basis of a description of a preferential embodiment of the invention, whereby reference is made to the following figures:

FIG. 1 renders an isometric view of a manipulator for application with a method or system according to the invention;

FIGS. 2a to 2c render a perspective view of three different positions of a table for a SEM sample and a brace for a TEM sample holder;

FIG. 3 renders a perspective view of part of the TEM sample holder according to FIGS. 2a to 2c, as well as a TEM disc;

FIG. 4 renders a perspective view of a table and TEM sample holder according to FIGS. 2a to 2c, in combination with an electron detection surface;

FIGS. 5a and 5b render schematic end views of a first position and a second position, respectively, of the manipulator according to FIG. 1;

FIGS. 6 to 13 render schematic isometric views of consecutive states involved in the removal of a sample from an object to be investigated;

FIGS. 14 to 16, and 17b, schematically depict further consecutive states subsequent to removal of the sample according to FIGS. 6 to 13, during which the sample is affixed to a TEM disc;

FIG. 17a renders a plan view of FIG. 17b.

FIG. 1 shows a manipulator 1 such as can be applied in the case of a method and a system according to the invention. The manipulator 1 is provided in the vacuum chamber of a SEM that, as a supplement to its standard embodiment, is provided with means for generating a Focused Ion Beam (FIB). A SEM embodied in this manner is also referred to using the term Dual Beam System. The electron beam and the ion beam intersect each other at an angle of circa 52 degrees at the location of a point of coincidence. By positioning an object to be investigated in this point of coincidence, the object to be studied can be processed with the ion beam, which processing can be imaged with the aid of the electron beam. The manipulator serves to position the object to be studied in a desired manner with respect to the electron beam and the ion beam. To this end, the object to be studied is positioned on a table 2 of the manipulator, which forms the extremity of a kinematic system with which table 2 can be moved in five degrees of freedom (three perpendicular translations and two rotations). To this end, the manipulator 1 comprises a manipulation body 3 that can be translated in two mutually perpendicular directions—depicted by arrows 4, 5 in FIG. 4—parallel to the upper surface of the table 2, and can also be rotated about the translation direction 4 as indicated by curved arrow 6, for which purpose the manipulator 1 is provided with a yoke, which is not further depicted. Furthermore, table 2 can be adjusted in height above manipulation body 3, as indicated by arrow 7, perpendicular to the plane of table 2, and can be rotated, as indicated by curved arrow 8, about an axis that coincides with the central axis of the disc-like table 2.

The manipulator 1 is of a so-called eucentric type, which, however, is not necessary within the context of the invention. In the case of eucentric manipulators, an object irradiated by the electron beam and the ion beam remains in focus during rotation according to arrow 6. The manipulator 1 described thus far already forms part of the prior art, and is thus well known to the skilled artisan, so that a further elucidation thereof within the context of the current invention can be omitted. Characteristic of the invention is, however, that, besides table 2, the manipulator 1 also comprises utilities 9 for positioning a TEM sample holder with a TEM sample attached thereto. Specific in this context is the requirement that these utilities leave space on the underside of the TEM sample for electrons that radiate through the TEM sample. Such a space is not present in the case of table 2. The utilities 9 comprise an essentially Ω-shaped brace 10 that is thus embodied that a TEM sample holder 11 can be connected thereto in a removable manner, which TEM sample holder is schematically depicted in FIGS. 2a to 2c, and 4. The TEM sample holder comprises a number of semi-circular hollows 12, which have a groove 13 along their circumferences. These grooves 13 make it possible to insert correspondingly formed semi-circular TEM discs 14 in a clamped manner in the hollows 12. The TEM discs 14 are themselves also provided with a series of hollows 15, arranged side-by-side; via a portion of the circumferential edge of these hollows 15, TEM samples 16 are connected to the TEM discs 14 in a manner that will be described later.

Although not strictly necessary in the context of the principal aspect of the present invention, but still very advantageous, the brace 10 can be rotated about the rotational axis 17. Rotational axis 17 is disposed parallel to the rotational axis indicated by curved arrow 6 such that, via rotation about both rotational axis 17 and the rotational axis indicated by curved arrow 6, a relatively large collective rotational range of more than 180 degrees is achieved, so that the TEM samples 16 can be perpendicularly irradiated by the electron beam on opposite sides of the samples. In the current, specific embodiment, brace 10 is rotatable about rotational axis 17 through a maximum of circa 120 degrees, whereas brace 10 can further rotate according to arrow 6 through a maximum angle of 70 degrees.

So as to effect rotation of table 2 according to curved arrow 8, the manipulation body 3 is provided with a cog 51 that is rotatable about its central axis as a result of being driven by driving means that are not further depicted, whereby the cog 51 is part of a transmission between the driving means and the table 2 for the purpose of rotating the latter. The side surface of cog 51 is engaged, at a distance from its central axis, by a driving rod 52, which in turn engages brace 10, at a distance from rotational axis 17, at the position of reference numeral 53. The connections between, on the one hand, the driving rod 52, and, on the other hand, the cog 51 and the brace 10, are such that mutual rotation is possible about axes parallel to the rotational axis 17. Rotation of cog 51 therefore causes both table 2 to rotate according to curved arrow 8 and brace 10 to rotate about rotational axis 17, the latter occurring back and forth through a rotational range of more than 180 degrees. In this manner, it becomes unnecessary to provide separate transmission and driving means for the special purpose of causing rotation of brace 10 about rotational axis 17, as a result of which brace 10 can, in principle, be added in a simple manner to an existing manipulator according to the prior art.

FIGS. 2a to 2c further depict the above-described principle in a somewhat different embodiment. In this scenario, a circular groove 54 is provided underneath table 2, which groove runs parallel to the upper surface of table 2. An endless transmission chord 55 is stretched around a large portion of this groove 54, which chord is also stretched about a round groove in a pressing roller 56. This pressing roller 56 presses chord 55 against the outer surface of a disc-like extremity 57 of a TEM sample holder 11, which, as a result hereof, shall rotate together with table 2 about an axis that coincides with the central axis of the disc-like extremity 57. As a result of this, a fixed relationship exists between the angular states of the table 2 and the TEM sample holder 11.

Underneath the TEM sample holder 11 is located a STEM detector disc 18 with which it is possible to observe electrons that have radiated through a TEM sample 16. The deflection suffered by these electrons as they radiate through the sample is a measure of the mass of the chemical elements of the TEM sample, and thus gives information on this mass. The skilled artisan is already familiar with STEM technology, which therefore does not require further elucidation here. The STEM detector disc 18 is carried by a composite carrying arm 19 that can be displaced along guide 20 in the direction of double arrow 21, which extends parallel to the direction indicated by arrow 5. Although the carrying arm 19 is regarded as being part of manipulator 1, it is not rigidly connected to manipulation body 3 thereof, so that, in principle, mutual movement is possible between the manipulation body 3 and the carrying arm 19.

For purposes of elucidation, one is directed to schematic FIGS. 5a and 5b. In FIG. 5a, the manipulator 1 is located in a first position, whereby the point of coincidence between the electron beam 22 and the ion beam 23 is located just above table 2, at a location where an object to be irradiated by the electron beam 22 and the ion beam 23 shall be positioned on the table 2. As will be elucidated later on the basis of FIGS. 6 to 13, it is possible in this first position of the manipulating means 1, and with the aid of the ion beam 23, to cut a (crude) TEM sample 16 away from its environment, which is formed by the remaining portion of the object carried on the table 2. In the first position, a stopping contact part 24 of carrying arm 19 is pushed against a stopping contact part 26 of manipulation body 3 as a result of the resilience of the pressing spring 25. After the (crude) TEM sample—cut off with the aid of the ion beam 23—has been removed completely from its environment, the manipulator 1 displaces itself to the second position according to FIG. 5b. During this displacement, the manipulation body 3 and the carrying arm 19 initially move collectively, due to the fact that pressing spring 25 forces stopping contact part 24 against stopping contact part 26. However, close to attainment of the second position according to FIG. 5b, a further stopping contact part 27 of carrying arm 19 impacts upon a fixed stopping contact part 28, which can be embodied as part of the manipulator arm 1 but which, as a result of its kinematic position, does not move together with manipulation body 3 thereof. As a result hereof, a certain play 29 arises between the stopping contact parts 24 and 26, which makes it possible, via limited displacement of the manipulation body 3 in the direction indicated by arrow 5 or in a direction opposite thereto, to mutually position, in a desired manner, the TEM sample holder 11—together, of course, with the various TEM samples 16—and the STEM detector disc 18.

Figure 14:
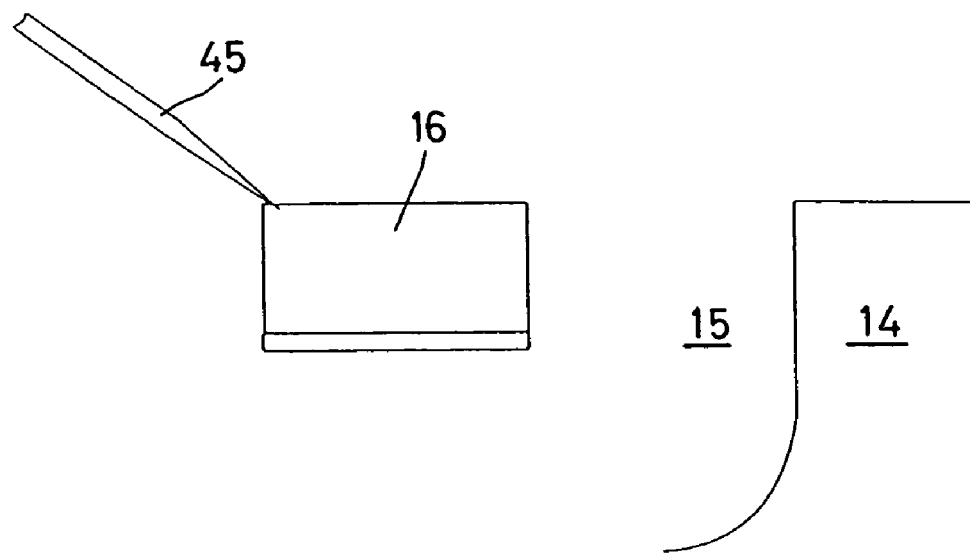
Figure 15:
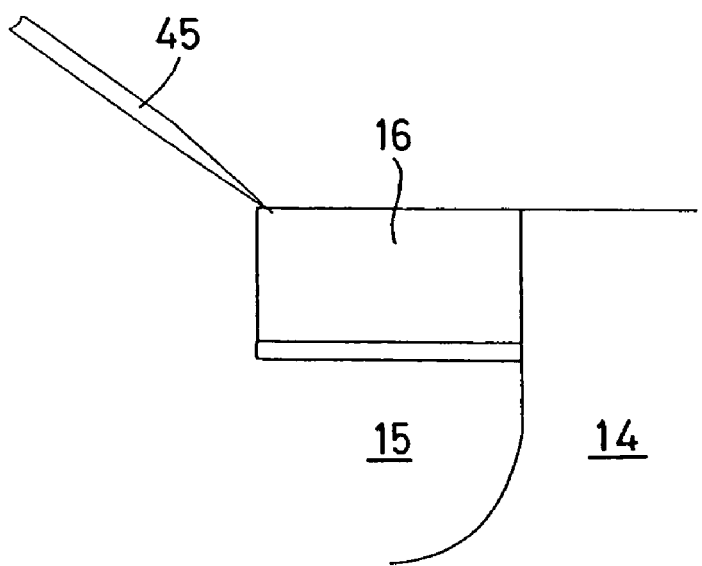
Figure 16:
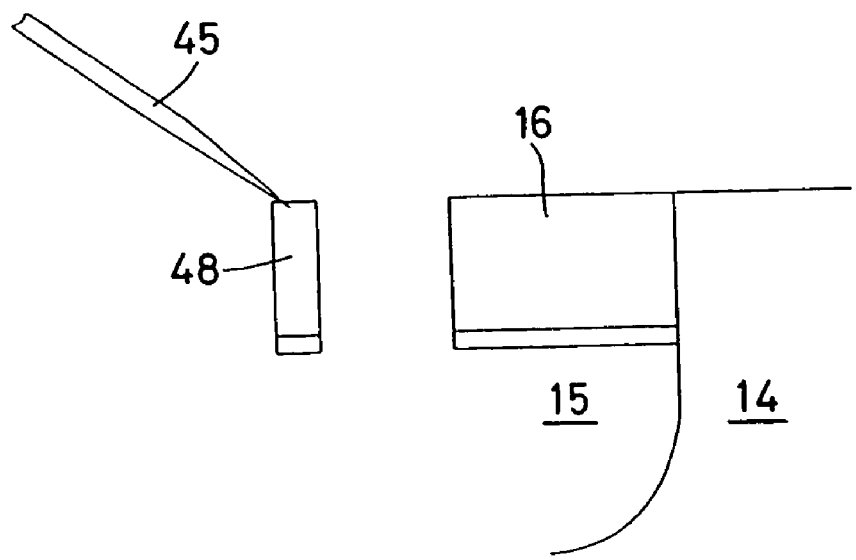

On the basis of FIGS. 6 to 17b, it will be subsequently explained how the particle-optical system, of which manipulator 1 is a part, can be applied. One starts off with a piece of material 30 that is carried by table 2. With the aid of an ion beam 23, one sequentially creates a number of perpendicular cutting planes 31, 32, and tilted cutting planes 33, 34. The respective upper cutting edges 35, 36, 37, 38 hereof extend parallel to one another. The tilted cutting planes 33, 34 extend beyond the respective perpendicular cutting planes 31, 32, and intersect one another between the perpendicular cutting planes 31, 32. Subsequently, ion beam 23 is employed to create a perpendicular cutting plane 39 along one side of the cutting planes 31, 32, 33, 34, the cutting plane 39 having an upper cutting edge 40 that extends perpendicular to the cutting edges 35, 36, 37, 38. In addition, at the opposite sides of the cutting planes 31, 32, 33 and 34, perpendicular cutting planes 41, 42, with respective upper cutting edges 43, 44, are respectively created (FIG. 10) between cutting plane 31 and 33 and between cutting plane 32 and 34. Subsequently, a probe 45, which in FIG. 11 and subsequent figures is transparently depicted, is attached via metal deposition to material 30, at the side of the cutting edge 40 between the cutting edges 35 and 36. The technology required for this procedure is known to the skilled artisan, e.g. from European patent application EP 927880 A1, and therefore requires no further elucidation here. After said attachment has been realized, a final perpendicular cutting plane 46, with upper cutting edge 47, is created using ion beam 23, which cutting plane 46 connects the cutting planes 41 and 42 to one another. As a result hereof, the portion of the material 30 that is principally located between the cutting planes 31 and 32 is freed from its environment, and can be regarded as (a crude form of) a TEM sample 16. This TEM sample 16 is lifted out of the material 30 with the aid of the probe 45, after which manipulator 1 displaces itself from the first position to the second position, as already set forth on the basis of the schematic FIGS. 5a and 5b. As a result of this, the TEM sample holder 11, in which the TEM discs 14 have been mounted in a clamped manner, assumes the approximate spatial position that, in the first position of the manipulator 1, was occupied by the table 2 thereof. In this second position, the probe 45 moves the TEM sample 16 against the circumferential edge of one of the hollows 15 in one of the TEM discs 14 (FIGS. 14 and 15). With the aid of metal deposition, the TEM sample 16 is attached to this circumferential edge, after which an extremal portion 48 of TEM sample 16, to which extremal portion the probe 45 is attached, is cut off (FIG. 16). If the TEM sample 16 satisfies the requirements for further investigation with the aid of the STEM detector disc 18, then such analysis can be performed immediately subsequent to the processing steps described heretofore. However, even if this were not the case, it is still possible as a supplementary step to further process the TEM sample 16 whilst attached to the TEM disc 14, principally by irradiation with an ion beam 23 so as to thin the sample, e.g. as is depicted in FIGS. 17a and 17b, whereby, on opposite sides of the TEM sample 16, material indicated by reference numerals 48 and 49 is removed, as a result of which a more thinned intermediate portion 50 arises, which can be subjected to transmissive irradiation using an electron beam 22.

An important advantage that is achieved thanks to the invention, of which a possible, non-limiting embodiment is described above, is manifested in the fact that both preparation of a TEM sample 16 and (transmissive) irradiation of the TEM sample 16 with an electron beam 22 can occur within one and the same vacuum chamber, as a result of which, on the one hand, the quality of the analysis shall generally improve, whereas, moreover, proportionately little time need be invested in such an analysis, which, above all, can be conducted by personnel with a lower level of training than the personnel that normally operates a TEM. However, this does not exclude the method and system according to the invention from being used to manufacture TEM samples that can be studied in a conventional manner in a TEM.

What is claimed is:

1. Method for the manufacture and transmissive irradiation of a sample, comprising the steps of:
   A Providing a particle-optical system having an internal low-pressure chamber and suitable for the generation of an electron beam and an intersecting ion beam in said chamber;
   B Providing a specimen within the chamber, carried by a manipulator;
   C Irradiating the specimen with the ion beam so as to cut a sample from the specimen;
   D Relatively displacing the sample thus cut to a sample holder than can be manipulated;
   E Attaching the sample to the sample holder; and
   F Using an electron beam to perform transmissive irradiation of the sample thus attached to the sample holder,
   characterized in that step F is performed in the low-pressure chamber of the particle-optical system according to step A.

2. Method according to claim 1, characterized in that, during step F, an electron detection surface is positioned at the side of the sample opposite to the surface upon which the electron beam impinges.

3. Method according to claim 1, characterized in that, after executing step E, the sample is irradiated with the ion beam, for the purpose of further processing the sample.

4. Method according to claim 1, characterized in that, after execution of step E, the sample holder is rotated about a rotational axis that is perpendicular to the electron beam and to the ion beam.

5. Method according to claim 4, characterized in that the rotational axis extends through the point of intersection of the electron beam and the ion beam.

6. Method according to claim 4, characterized in that rotation about the rotational axis is performed, in combination with rotation of the sample holder about a manipulator rotational axis that extends parallel to said rotational axis, through a range of at least 180 degrees.

7. Particle optical system, comprising a low-pressure chamber containing manipulator means for at least two objects to be irradiated, an electron source and an ion source for the purpose of allowing irradiation of an object, carried by the manipulating means, using an electron beam and an ion beam, respectively, the manipulating means comprising a number of first manipulation parts, which are movable relative to one another and collectively movable relative to the electron beam and the ion beam according to a first set of degrees of freedom, one of which first manipulation parts comprising a first object carrier, for allowing, in the case of a first object carried by the first object carrier and at a first position of the manipulating means, reflective irradiation of said first object using an electron beam and/or irradiation of said first object using an ion beam, the manipulating means further comprising at least one second manipulation part comprising a second object carrier, the system further comprising displacing means for relatively displacing an object from the first object carrier to the second object carrier, characterized in that the manipulating means are embodied so as to allow, in the case of a second object carried by the second object carrier and at a second position of the manipulating means, transmissive or reflective irradiation of said second object by an electron beam and/or irradiation of said second object by an ion beam.

8. System according to claim 7, characterized in that the second manipulation part is movable in at least one further degree of freedom with respect to the electron beam and the ion beam, as well as with respect to a remaining portion of the manipulating means.

9. System according to claim 8, characterized in that the at least one further degree of freedom is a rotation about a rotational axis that extends perpendicular to the electron beam and to the ion beam.

10. System according to claim 9, characterized in that the rotation about the rotational axis can occur through a range of at least 180 degrees, combined, if desired, with rotation about a manipulator rotational axis that extends parallel to said rotational axis.

11. System according to claim 10, characterized in that the rotational axis extends through the point of intersection of the electron beam and the ion beam.

12. System according to claim 8, characterized in that the motion according to said at least one further degree of freedom can only occur in combination with motion according to one degree of freedom of the first set of degrees of freedom.

13. System according to claim 7, characterized in that the system comprises an electron detection surface at the side of the second object—carried by the second object holder—that is remote from the electron beam.

14. System according to claim 13, characterized in that the electron detection surface is collectively movable with the manipulating means in the direction extending between the first position and the second position of the manipulating means.

15. System according to claim 14, characterized in that the electron detection surface and the manipulating means are movable independently of one another in the direction extending between the first position and the second position of the manipulating means.

16. System according to claim 14, characterized in that a spring means causes the electron detection surface to move together with the manipulating means from the first position to the second position, and a stopping contact between the manipulating means and a part rigidly connected to the electron detection surface causes the electron detection surface to move together with the manipulating means from the second position to the first position.

17. System according to claim 16, characterized in that, in the second position of the manipulating means, there is play between the manipulating means and the part rigidly connected to the electron detection surface.

18. Method according to claim 2, characterized in that, after executing step E, the sample is irradiated with the ion beam, for the purpose of further processing the sample.

19. Method according to claim 3, characterized in that, after execution of step E, the sample holder is rotated about a rotational axis that is perpendicular to the electron beam and to the ion beam.

20. System according to claim 9, characterized in that the motion according to said at least one further degree of freedom can only occur in combination with motion according to one degree or the first set of degrees of freedom.

21. System according to one of the claim 8, characterized in that the system comprises an electron detection surface at the side of the second object—carried by the second object holder—that is remote from the electron beam.

22. System according to one of the claim 9, characterized in that the system comprises an electron detection surface at the side of the second object—carried by the second object holder—that is remote from the electron beam.

23. System according to claim 15, characterized in that a spring means causes the electron detection surface to move together with the manipulating means from the first position to the second position, and a stopping contact between the manipulating means and a part rigidly connected to the electron detection surface causes the electron detection surface to move together with the manipulating means from the second position to the first position.

24. A particle optical system for extracting a sample from a work piece and transmitting electrons through the sample, comprising:
   a stage for supporting a work piece;
   an ion beam column for producing an ion beam to cut a sample from the work piece, the ion beam column having an ion beam axis;
   a sample manipulator for repositioning the sample cut from the work piece by the ion beam column;
   an electron beam column for producing an electron beam for transmitting through the sample, the electron beam column having an electron beam column axis; and
   an electron detector positioned to detect electrons transmitted through the sample,
   the stage, the ion beam column, the electron beam column, the sample manipulator and the electron detector being positioned in a low pressure chamber to allow the sample to be cut, repositioned and have electrons transmitted through the sample and detected, without removing the sample from the vacuum chamber.

25. The particle optical system of claim 24 in which the ion beam axis is tilted with respect to the electron beam axis.

26. The particle optical system of claim 25 in which the electron beam axis is substantially vertical.

27. The particle optical system of claim 25 in which the ion beam and the electron beam are substantially coincident on the work piece surface.

28. The particle optical system of claim 24 in which the stage can be tilted.

29. The particle optical system of claim 24 further comprising a sample holder for holding the sample while transmitting the electron beam through the sample, the sample holder allowing electrons in the beam to reach the electron detector.

30. The particle optical system of claim 29 further comprising a movable support for selectively positioning either the stage or the sample holder under the electron beam to allow the electron beam to impact the work piece or the sample.

31. The particle optical system of claim 29 in which the sample holder includes positions for holding multiple samples.

32. The particle optical system of claim 29 in which the sample holder is rotatable to facilitate attaching samples using the sample manipulator and viewing samples.

33. The particle optical system of claim 29 in which the sample manipulator can reach the work piece and the sample holder, so that the sample manipulator can transport the cut sample from the work piece to the sample holder.

34. The particle optical system of claim 29 in which the stage and the sample holder are positioned on a first movable assembly and the electron detector is moveable relative to sample holder.

35. The particle optical system of claim 34 in which the electron detector is mounted on a second movable assembly, the second movable assembly being biased against the first moveable when positioned such that the ion beam and the electron beam can impact the work piece.

36. A method of extracting a small sample and transmitting electrons through the sample within a low pressure chamber, comprising:
   cutting a sample from a work piece using a focused ion beam in the low pressure chamber;
   moving the sample from the work piece to a sample holder in the low pressure chamber;
   attaching the sample to the sample holder in the low pressure chamber; and
   directing an electron beam toward the sample in the sample holder in the low pressure chamber; and
   detecting electrons transmitted through the sample in the low pressure chamber.

37. The method of claim 36 in which cutting a sample using a focused ion beam includes directing an ion beam toward the work piece surface along a first direction and in which directly an electron beam to the sample includes directing an electron beam toward the sample along a second direction that is nor parallel to the first direction.

38. The method of claim 37 in which the electron beam and the ion beam impact at approximately the same spot on the work piece.

39. The method of claim 36 further comprising detecting secondary electrons to form an image of the work piece or the sample.

40. The method of claim 36 in which directing detecting electron transmitted though the sample includes moving an electron detector relative to the sample holder to position the electron detector under the sample.

* * * * *